United States Patent [19]
Billotti

[11] Patent Number: 5,588,956
[45] Date of Patent: Dec. 31, 1996

[54] METHOD FOR SUPPORTING BODY JOINTS AND BRACE THEREFOR

[76] Inventor: Joseph D. Billotti, 18 Powder Hill, Saddle River, N.J. 07458

[21] Appl. No.: 442,782

[22] Filed: May 17, 1995

Related U.S. Application Data

[60] Continuation-in-part of Ser. No. 366,316, Dec. 29, 1994, Pat. No. 5,527,267, which is a division of Ser. No. 137,830, Oct. 15, 1993, Pat. No. 5,378,224, which is a continuation-in-part of Ser. No. 73,722, Jun. 9, 1993, abandoned.

[51] Int. Cl.⁶ .................................................. A61F 5/00
[52] U.S. Cl. .......................... 602/13; 602/26; 602/62; 128/DIG. 20
[58] Field of Search .................................... 602/5, 13, 19, 602/26, 27, 61–63; 128/DIG. 20; 601/148, 151

[56] References Cited

U.S. PATENT DOCUMENTS

| | | |
|---|---|---|
| D. 307,054 | 4/1990 | Johnson, Jr. . |
| 2,823,668 | 2/1958 | Van Court et al. . |
| 3,186,404 | 6/1965 | Gardner . |
| 3,548,420 | 12/1970 | Spence . |
| 3,553,123 | 1/1971 | Moore . |
| 3,741,203 | 6/1973 | Liman . |
| 3,937,218 | 2/1976 | Gaylord, Jr. . |
| 3,939,829 | 2/1976 | Spann . |
| 3,955,565 | 5/1976 | Johnson, Jr. . |
| 4,084,584 | 4/1978 | Detty . |
| 4,182,340 | 1/1980 | Spencer . |
| 4,219,892 | 9/1980 | Rigdon . |
| 4,263,905 | 4/1981 | Couch, Jr. . |
| 4,280,489 | 7/1981 | Johnson, Jr. . |
| 4,287,920 | 9/1981 | Johnson, Jr. . |
| 4,296,744 | 10/1981 | Palumbo . |
| 4,378,009 | 3/1983 | Rowley et al. . |
| 4,508,112 | 4/1985 | Seeler . |
| 4,539,982 | 4/1985 | Bailly . |
| 4,597,384 | 7/1986 | Whitney . |
| 4,628,918 | 12/1986 | Johnson, Jr. . |
| 4,628,945 | 12/1986 | Johnson, Jr. . |
| 4,669,455 | 1/1987 | Bellati . |
| 4,700,698 | 10/1987 | Kleylein . |
| 4,703,750 | 11/1987 | Sebastian et al. . |
| 4,730,610 | 3/1988 | Graebe . |
| 4,872,445 | 10/1989 | Johnson, Jr. . |
| 4,926,884 | 5/1990 | Lonardo . |
| 4,938,207 | 7/1990 | Vargo . |
| 4,953,569 | 9/1990 | Lonardo . |
| 4,961,415 | 10/1990 | McLaurin-Smith . |
| 5,024,216 | 6/1991 | Shiono . |
| 5,113,877 | 5/1992 | Johnson, Jr. . |
| 5,125,400 | 6/1992 | Johnson, Jr. . |
| 5,230,695 | 7/1993 | Silver et al. . |
| 5,277,697 | 1/1994 | France et al. . |
| 5,288,286 | 2/1994 | Davis et al. . |
| 5,334,135 | 8/1994 | Grim et al. . |
| 5,378,224 | 1/1995 | Billotti . |
| 5,383,843 | 1/1995 | Watson et al. . |
| 5,385,538 | 1/1995 | Mann . |

OTHER PUBLICATIONS

How To Choose A Garden Hose, Consumer Reports May 1993, pp. 290–291.

*Primary Examiner*—Linda C. Dvorak
*Attorney, Agent, or Firm*—Arthur Jacob

[57] ABSTRACT

The invention is directed toward providing a method and a brace for supporting a knee joint to permit movement of the joint in first selected directions and to restrain movement in second selected directions. The brace comprises a flexible sheet and at least two enclosed inflatable chambers contained in the flexible sheet. The chamber is formed of a material which is light and flexible when uninflated but is relatively rigid when inflated. Each inflated chamber follows a path corresponding to that of one of the cruciate ligaments and together they support the joint and prevent unwanted movement of the portion to be restrained from movement. However, the material has sufficient flexibility and when coupled with the flexible sheet serves to prevent abrasion of the sensitive areas of the joint being confined. The flexible sheet, while very flexible, also protects against the transmission of shock to the joint.

10 Claims, 13 Drawing Sheets

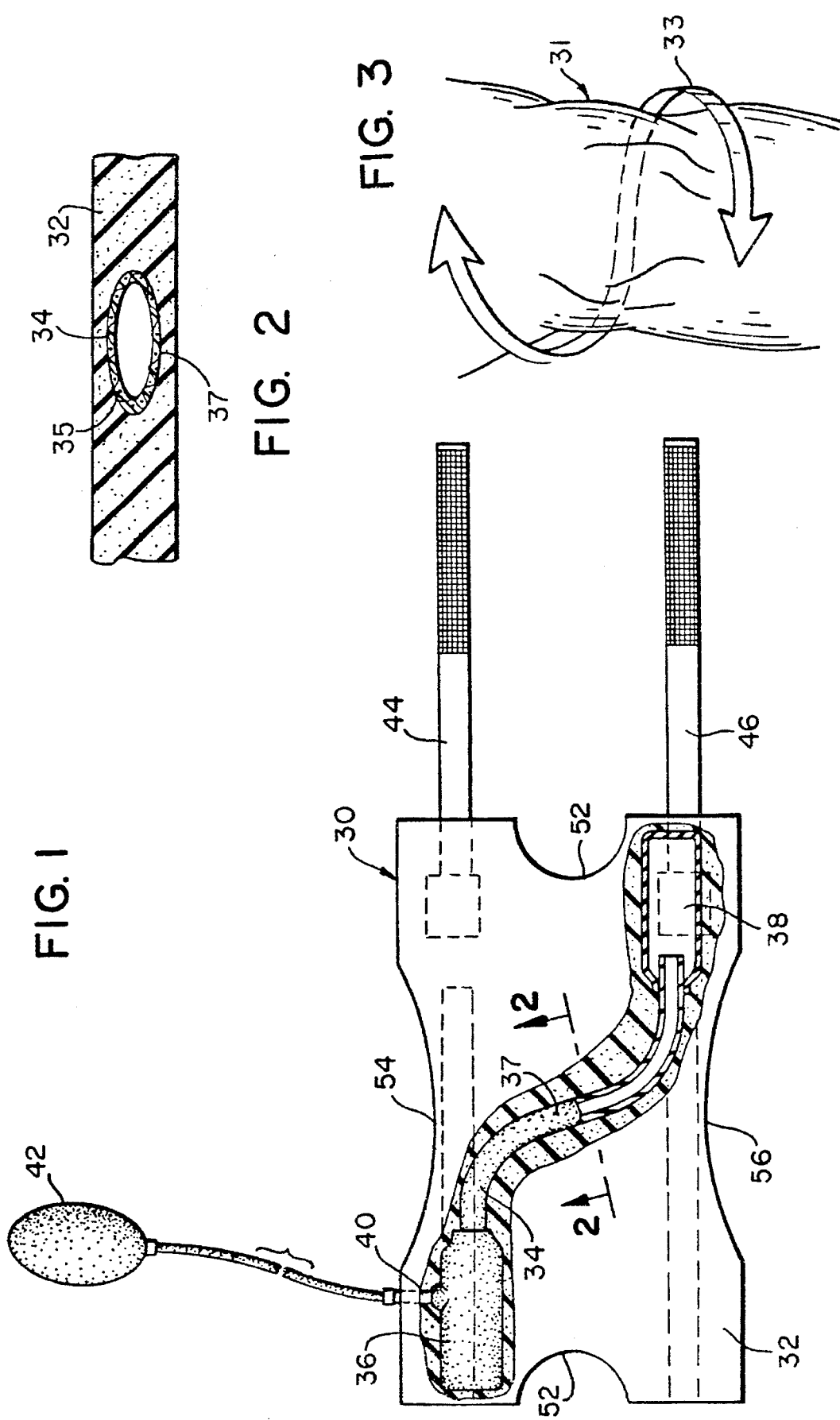

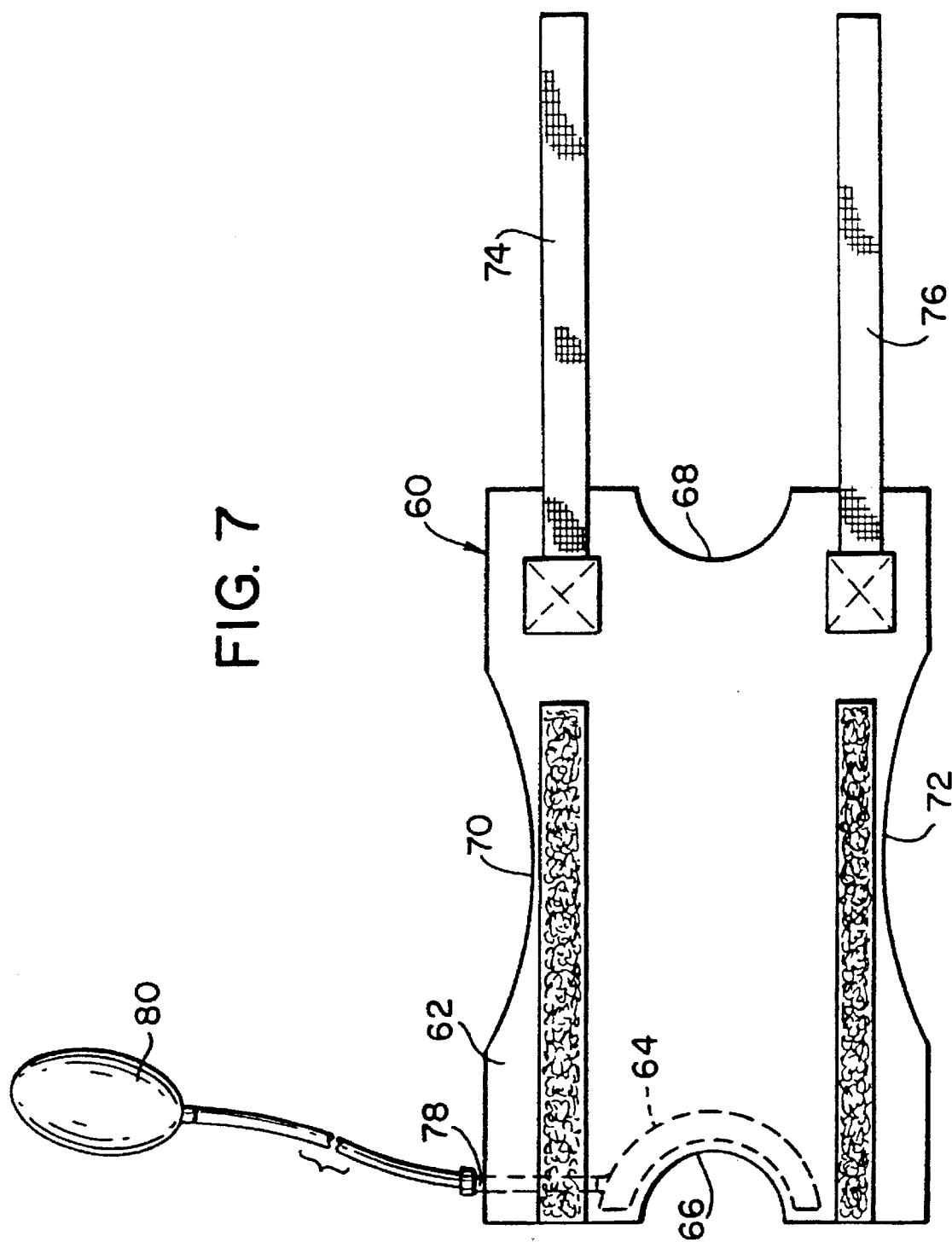

5,588,956

METHOD FOR SUPPORTING BODY JOINTS AND BRACE THEREFOR

This is a continuation-in-part of application Ser. No. 08/366,316, filed Dec. 29, 1994, now U.S. Pat. No. 5,527,267, which is a division of application Ser. No. 08/137,830, filed Oct. 15, 1993, now U.S. Pat. No. 5,378,224, issued Jan. 3, 1995, which is a continuation-in-part of application Ser. No. 08/073,722, filed Jun. 9, 1993, now abandoned.

The invention relates to a brace and a method for supporting a joint of the body so as to permit freedom of movement in a first selected direction while precluding or inhibiting movement in a second selected direction. Braces are commonly used, for example, on knees and ankles as well as on other joints of the body. Some braces are used to support weak joints to prevent further destruction and/or to support a joint during exercise or normal activity. Others are used to limit movement in weakened areas of the joint while permitting free movement in other areas of the joint to prevent deterioration of the undamaged portion of the joint. Two joints which require correction at the present time due to, for example, sports activity, accidents and deterioration due to aging deterioration, are the knee and the ankle.

The brace of the invention possesses certain basic elements to support a joint and the joint areas to strengthen the weakened portion of the joint while preventing abrasion of the skin or exposed areas of the joint in the supported member. The basic method and the structure of the brace of the invention may be used in the treatment of ailments of various joints of the body. However, the configuration of the device must be made to accomplish the desired curative results with differing location and shape of the elements making up the structure of the brace of the invention.

Each embodiment of the invention shown and described herein serves to follow this essential characteristic while, at the same time, changing the shape and/or the structural elements in order to accomplish the corrective and curative powers required in the particular situation.

It is a principal object of the invention to provide a system and a method for supporting a joint of the body to accomplish the appropriate corrective and curative effects that are necessary and desired.

It is a further object of the invention to prevent abrasion of the skin and other portions of the body with which the brace comes into contact.

It is another object of the invention to provide the brace with a flexible sheet construction to prevent such abrasion.

It is yet another object of the invention to provide a support member contained within the flexible sheet for the weakened portion of the joint in the form of at least one inflatable chamber which is flexible while the brace is being applied to the joint and which supports a weakened portion of the joint after it has been inflated.

It is a still further object of the invention to provide such an inflatable chamber having a construction which is reasonably strong and, when inflated, is relatively rigid so as to support the portions of the joint which need support, yet will have some desired flexibility under stress. As an example, the material presently used for bicycle tire inner tubes is serviceable for this purpose.

These and other objects, advantages, features and uses will be apparent during the course of the following description when taken in conjunction with the accompanying drawing in which:

FIG. 1 is a plan view of an embodiment of the invention for supporting the knee having weakness of at least one of the cruciate ligaments;

FIG. 2 is an enlarged view, in cross-section, taken along the line 2—2 of FIG. 1;

FIG. 3 is a diagrammatic view of the path of the support element when applied to a knee to correct cruciate ligament weakness;

FIG. 7 is a view similar to that of FIG. 1 of a brace of the invention for correcting chondromalacia patellae of the knee;

Figure 4:
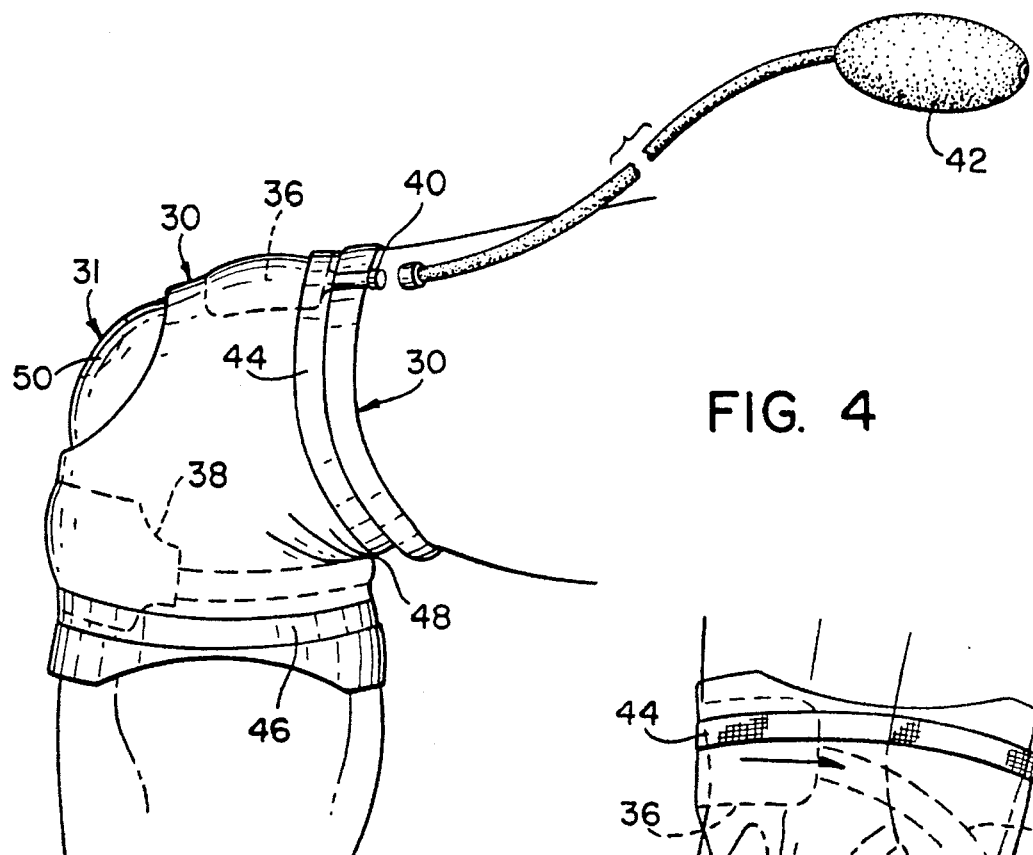
FIG. 4 is a medial view of a flexed knee showing the brace of the invention of FIG. 1, applied thereto.

Preferred embodiments of the invention are illustrated in the accompanying drawing. All of the embodiments shown in the drawing and described in the description utilize the same inventive concept.

SUPPORT FOR CRUCIATE LIGAMENT DAMAGE

In FIG. 1, the numeral 30 designates a brace of the invention, generally. Brace 30 is designed for use in the correction of damage or weakness of the cruciate ligament and is seen to include a flexible sheet 32 constructed of an elastomeric sheet of silicone polymer or similar material. Flexible sheet 32 is extremely flexible and pliable to prevent abrasive damage to a knee when the brace is placed on it. Within flexible sheet 32 there is enclosed an inflatable member or chamber 34. Chamber 34 is formed of soft rubber or similar material which is relatively stiff when inflated. Such materials are presently used in bicycle tire inner tubes and in certain garden hoses.

Inflatable chamber 34 is seen to be generally sinuous in shape and is provided with two enlarged chambers, one at each end of the sinuous, medial portion 37 of the chamber 34. These enlarged chambers are designated by numerals 36 and 38. A valve 40 is connected to inflatable chamber 34, as shown, for example, at enlarged chamber 36. When the brace 30 is applied to a knee, the chamber 34 is inflated to the desired hardness by means, for example, of a hand pump 42. After the inflation process is completed, the hand pump 42 is removed. Valve 40 is of the type which remains closed when the hand pump 42 is removed so that the inflatable chamber 34 remains inflated.

The numeral 31 generally designates a knee which is being treated for weakness of the cruciate ligament and the sinuous arrows 33 of FIG. 3 illustrate the path of the inflatable chamber 34 when it is applied to knee 31. The medial portion 37 of inflatable chamber 34 may be made of two types of structure, depending upon the corrective procedure which is required. In one case, the medial portion 37, which is an integral part of inflatable chamber 34, is formed of soft rubber or similar material. In the second case, in which a greater amount of support of the popliteal fossa 48 of the knee is required (FIG. 4) a portion of medial portion 37 is reinforced at the popliteal fossa 48 under the area requiring additional support. Such support may be attained by reinforcing the medial portion 37 with a mesh 35 of light metal or plastic webbing embedded within the medial portion 37, as seen in FIG. 2.

In FIG. 4, knee 31 is shown in its flexed position with brace 30 applied. The patella 50 of knee 31 is exposed to the atmosphere to minimize the effort of walking with the brace 30 affixed. This exposure of the patella 50 is accomplished by providing an opening 52 in sheet 32 (see the plan view of the brace 30 in FIG. 1). Also shown in FIG. 1 are shaped areas 54 and 56 to accommodate smooth application to the proximal and distal portions, respectively, of the knee 31. A pair of straps 44 and 46, preferably equipped with hook and loop fasteners, such as those commonly known as VELCRO fasteners, are used to hold the brace 30 in place on the knee 31.

Figure 5:
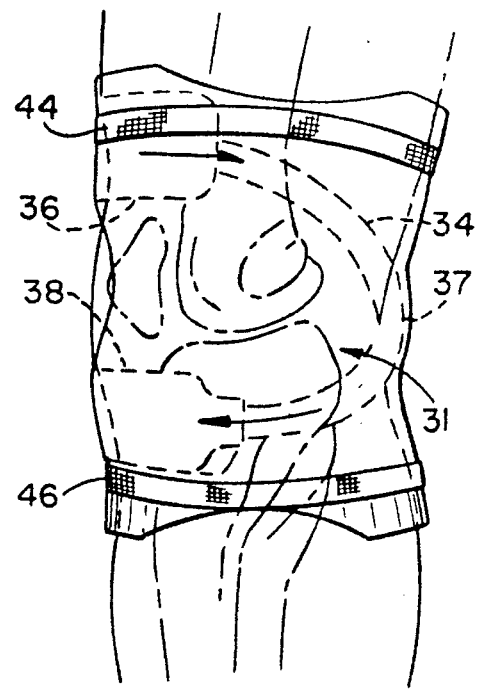
FIG. 5 is a medial view of the knee of FIG. 4 in its extended position.
Figure 6:
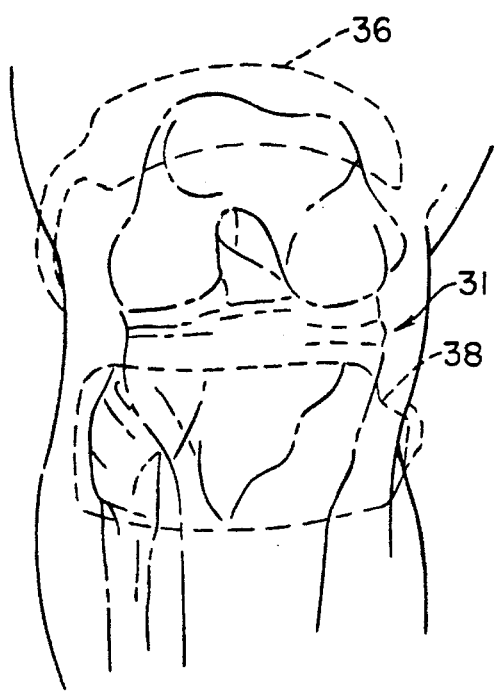
FIG. 6 is an anterior view of the knee of FIG. 4 in its flexed position (patella not shown)

FIG. 5 is an extended medial view of knee 31 with the brace 30 removed to show the anatomical portions of the knee 31 with the inflatable chamber 34 and its components shown in dashed lines. Straps 44 and 46 are also shown to illustrate their positions when the knee 31 is extended. FIG. 6 is an anterior view of knee 31 in its flexed position with the patella not shown. The positions of the enlarged portions 36 and 38 of the inflatable member 34 are shown in dashed lines.

In use, the brace 30 is wrapped loosely around the knee 31 so that inflatable chamber 34 follows the path of arrows 33 of FIG. 3 and is positioned so that enlarged portions 36 and 38 will support the weakened area properly. Now, pump 42 is connected to valve 40 and chamber 34 is inflated to its proper pressure. The straps 44 and 46 are tightened and the pump 42 is removed from the valve 40. Since valve 40 is normally closed, the chamber 34 will remain inflated. Other pumps may be substituted for the hand pump 42 illustrated in the figures.

After the brace 30 is in place, it will support the area which must have its motion inhibited and will permit freedom of motion of the elements which are not required to be restricted in movement. The inflatable chamber 34 serves to support the selected portions of the knee 31 because of the substantially rigid condition of its outer surface, when inflated. However, abrasion to the knee 31 is minimized because of the extreme flexibility of the surrounding flexible sheet 32 which, in this instance, is formed of an elastomer such as a silicone polymer or a similar elastomeric material. Such materials are very soft, non-abrasive and very flexible so that there is little or no adverse effect on the outer surface of the knee 31.

BRACE FOR CHONDROMALACIA OR PATELLAE SUBLUXATION (SLIPPAGE)

Chondromalacia, also known as patellae subluxation (slippage) has many causes. It is a slippage of the patella due, perhaps, to tilting of the kneecap resulting from the fact that the knee is flexed more than it is straight. As a result, the patella articulates with the lateral condyle of the distal femur instead of sliding over it smoothly.

Figure 9:
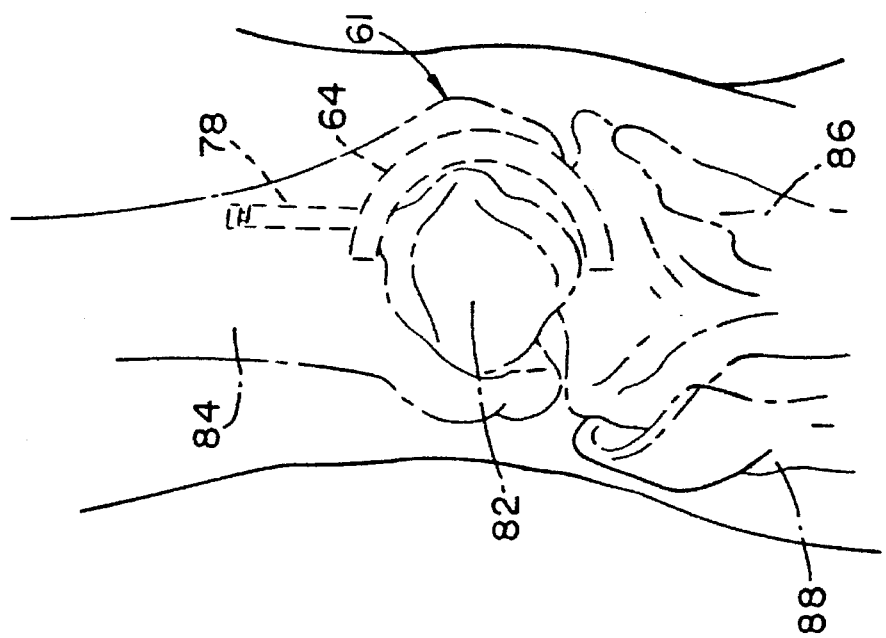
FIG. 9 is view of the knee of FIG. 8, with the brace removed, showing the position of the support member of the brace in dashed lines.
Figure 8:
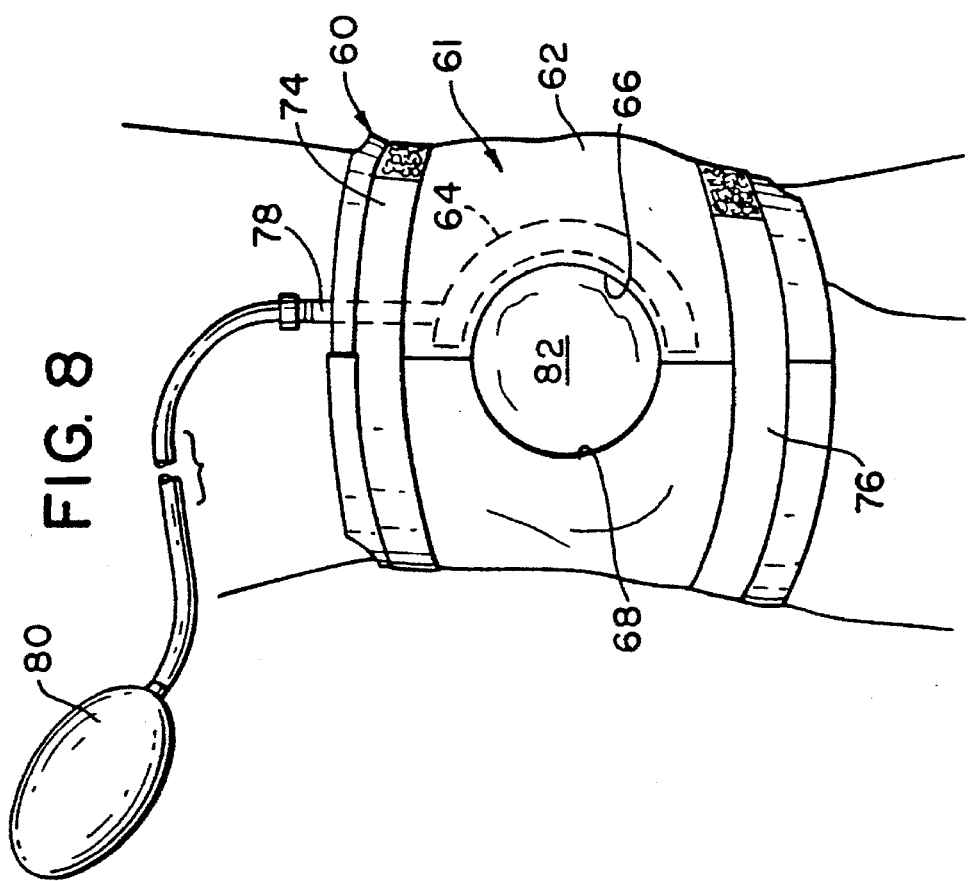
FIG. 8 is a front view showing the brace of FIG. 7 applied to a knee.
Figure 10:
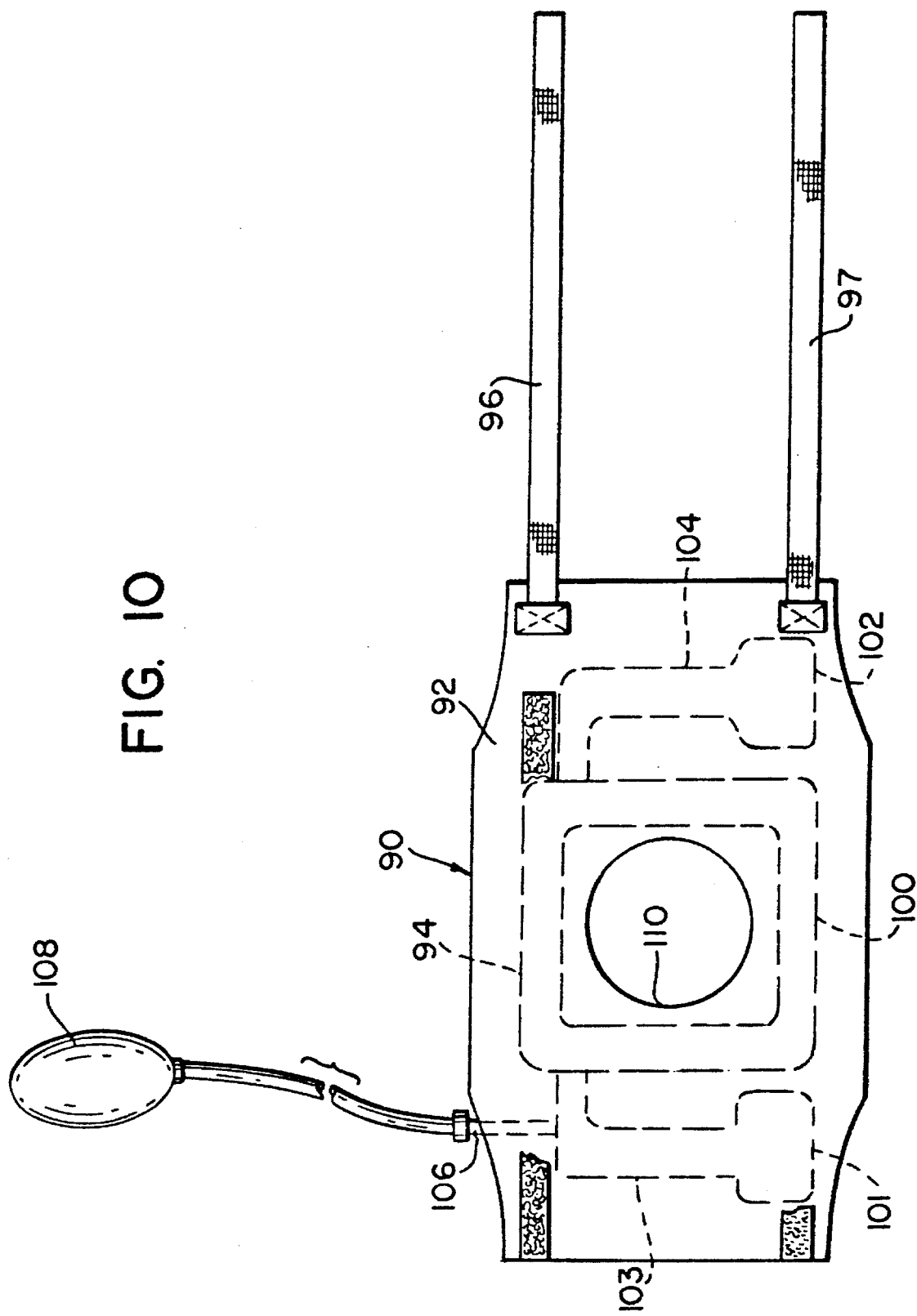
FIG. 10 is a view similar to that of FIG. 1 of a brace of the invention for correcting knee instability.
Figure 11:
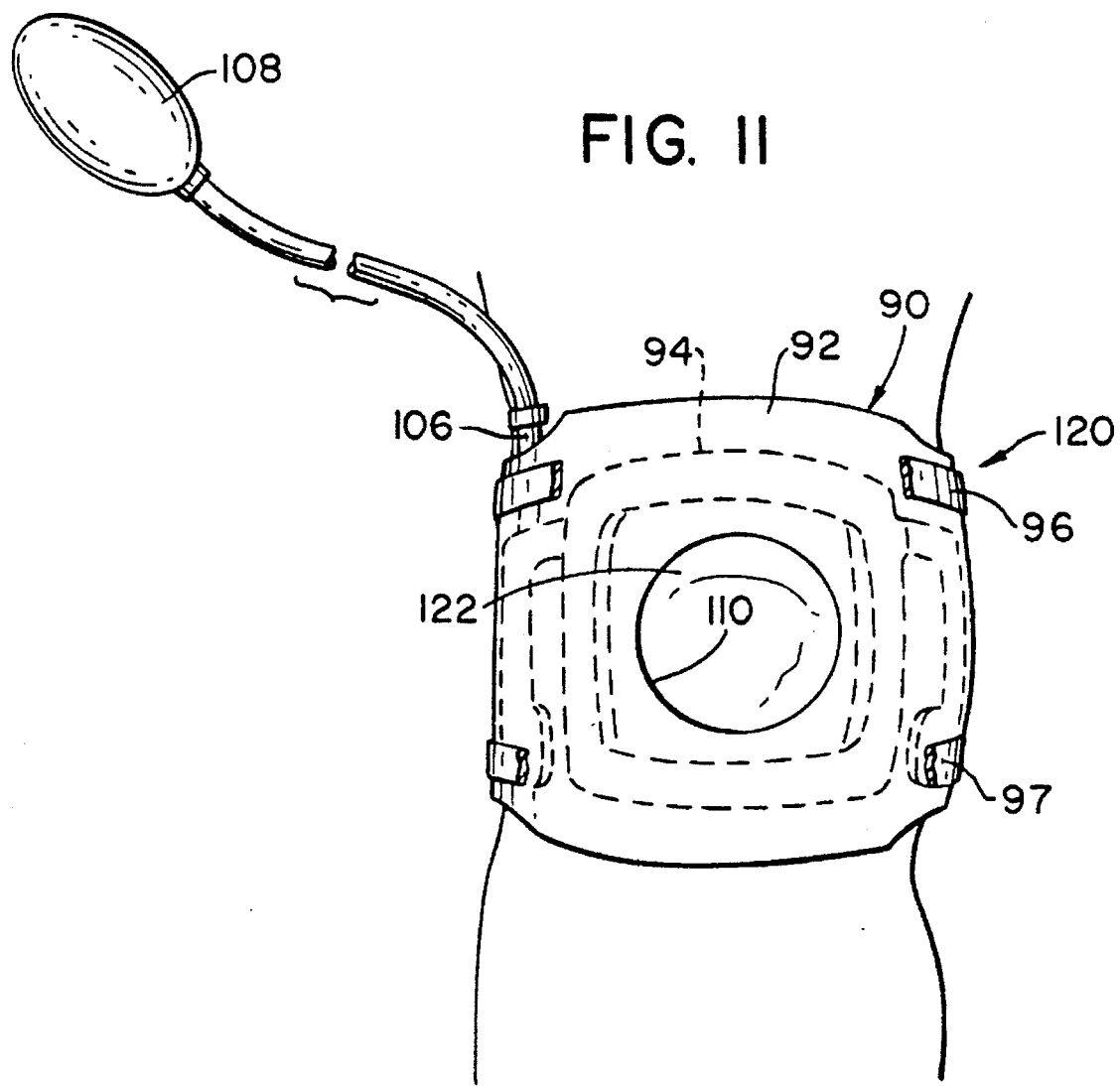
FIG. 11 is a view of the brace of FIG. 10 applied to a knee (anterior view—extended)
Figure 12:
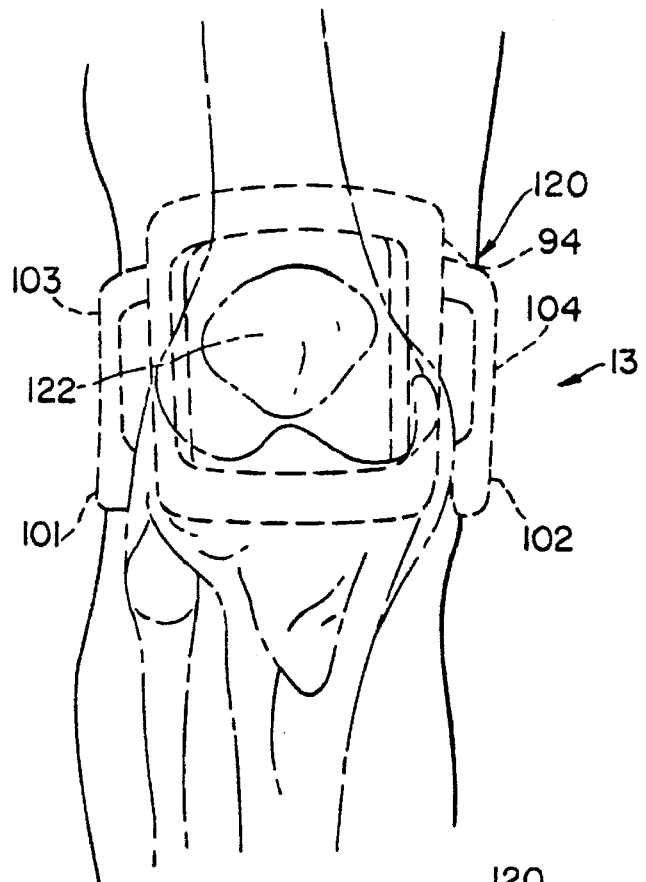
FIG. 12 is a view similar to that of FIG. 11 with the brace removed showing the position of the support member in dashed lines.
Figure 13:
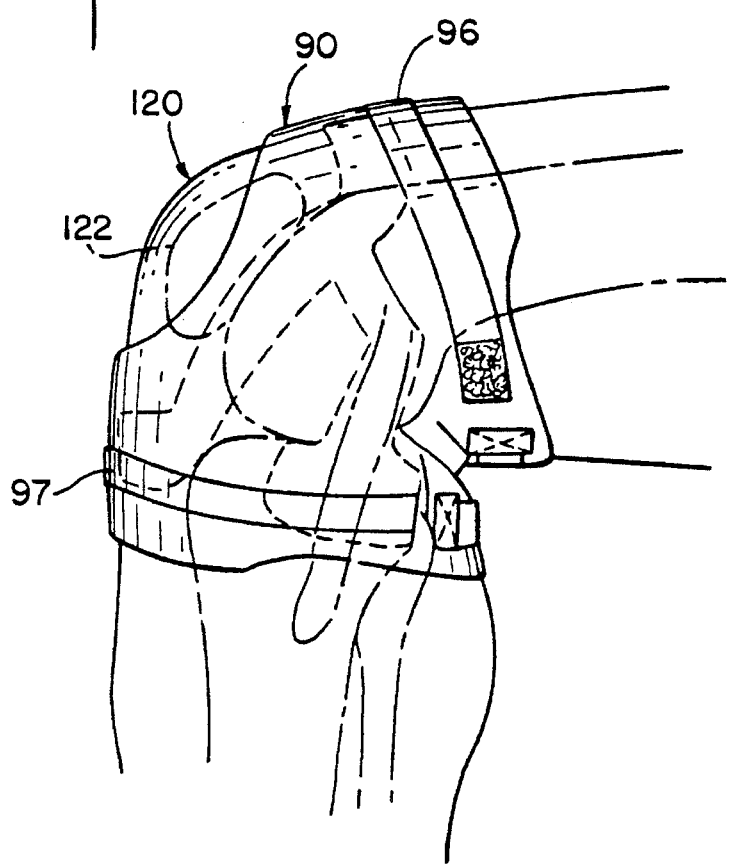
FIG. 13 is a medial view of the flexed knee of FIG. 12 in the direction of arrow 13 of FIG. 12 showing the tibial collateral ligament with the support member in dashed lines.
Figures 14, 15:
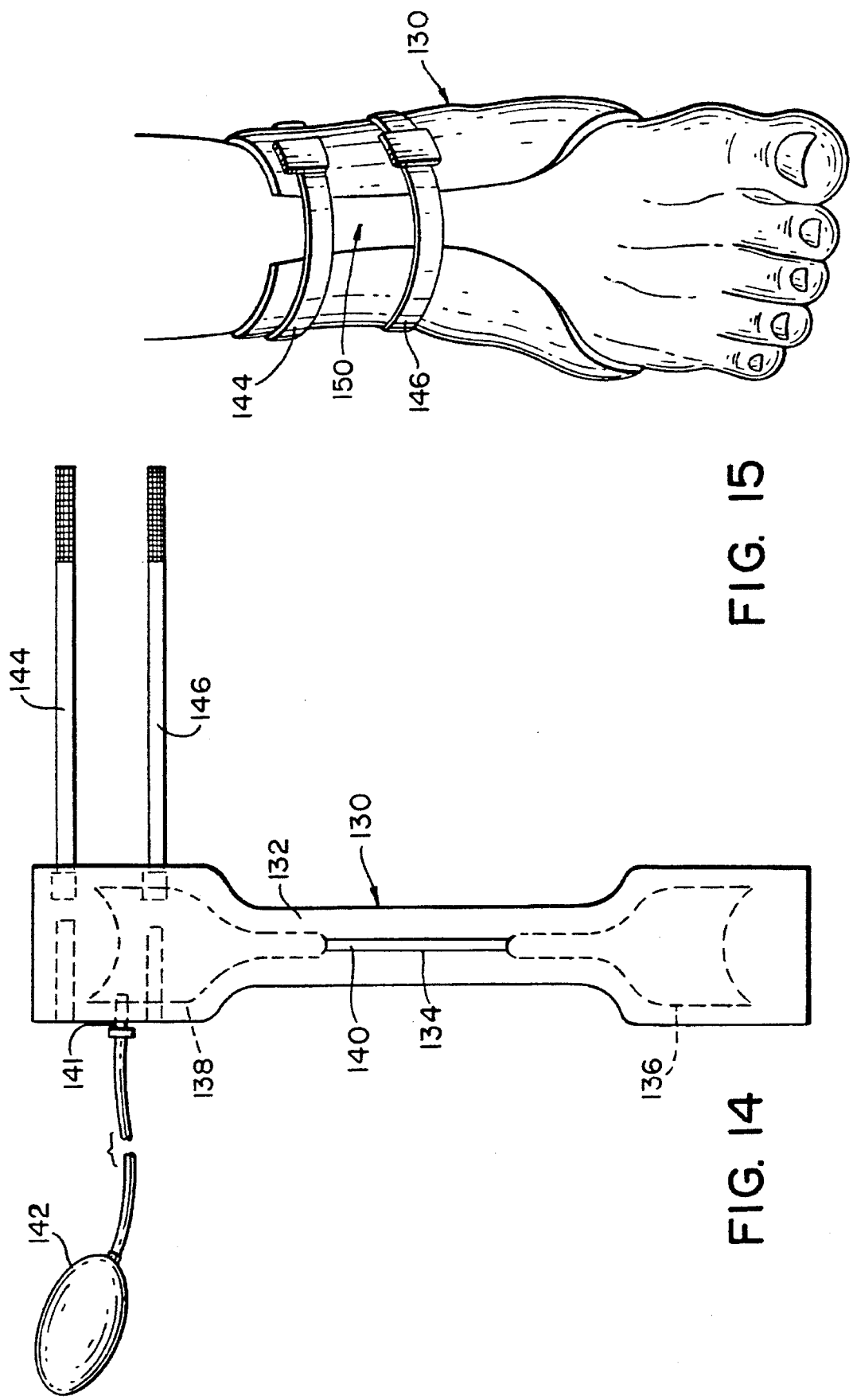
FIG. 14 is a view similar to that of FIG. 1 of an ankle brace to protect the ankle after surgery or other corrective procedure on the ankle bones.
FIG. 15 is a front view of an ankle with the brace of FIG. 14 applied thereto.

In FIGS. 7 through 9 there is shown a brace 60 which is seen to comprise a flexible sheet 62, in this instance constructed of an elastomeric material such as a silicone polymer, and an arcuate, inflatable chamber 64 located within flexible sheet 62. Arcuate shaped areas 66 and 68 are placed at opposite ends of the flexible sheet 62 to provide an opening for the patella when brace 60 is applied to a knee 61, as set forth below. The longer sides of sheet 62 are shaped as shown at 70 and 72 to fit properly to the proximal and distal areas, respectively, of the knee 61 when the brace 60 is applied to knee 61. Straps 74 and 76, which are preferably provided with VELCRO fasteners, are used to hold the brace 60 on the knee 61. As before, a valve 78 communicates with inflatable chamber 64 and a pump 80 selectively is connected to the valve 78.

Knee 61 is seen to have a patella 82 (FIGS. 8 and 9). In FIG. 8, the brace 60 is shown applied to the knee 61 and the arcuate, inflatable chamber 64 is seen to be juxtaposed with the patella 82 so as to support it. The view of FIG. 9 is similar to that of FIG. 8 and shows the knee 61 with the brace 60 removed and the position of the inflatable chamber 64 shown in dashed lines as it is in FIG. 8.

The patella 82 of knee 61 is shown in FIG. 9 to be connected to a femur 84, a tibia 86 and a fibula 88. The figure shows the relation of the inflated chamber 64 to the brace 60 with respect to the elements of the knee and leg.

When the brace 60 is in place, the inflatable chamber 64 serves to keep patella 82 from tilting and slipping so that the pain from walking and using stairs is reduced considerably. To make the installation on the knee 61, the brace 60 is placed on the knee 61 and is wrapped around it. Then, the inflatable chamber 64 is inflated and when the proper amount of pressure is attained, the pump 80 is removed from the valve 78 and the chamber 64 remains inflated. Now, straps 74 and 76 are wrapped firmly around the knee 61 to hold the brace 60 in place.

BRACE TO CONTROL KNEE INSTABILITY

In FIGS. 10 through 13, there is illustrated a brace 90 of the invention for controlling and positioning a knee 120 to overcome instability due to weakness of the fibular and/or the tibial collateral ligaments. Brace 90 is seen to comprise a flexible sheet 92, shown in the form of a silicone polymer or similar elastomeric material, with an inflatable chamber 94 enclosed within the flexible sheet 92. A pair of straps 96 and 97 serve to hold the brace 90 in place on a knee 98. The straps 96 and 97 are preferably provided with VELCRO fasteners.

Inflatable chamber 94 is seen to comprise an annular section 100 which is generally polygonal in shape and a pair of enlarged sections 101 and 102 which are connected to the annular section 100 by channels 103 and 104, respectively. A valve 106 is connected to the inflatable chamber 94 at, for example, channel 103. A pump 108 is connected to a valve 106 to inflate the inflatable chamber 94 to the proper pressure and is then removed from the valve 106. Upon removal of the pump 108 from the valve 106, the valve 106 closes and the inflatable chamber 94 remains in its inflated condition.

This embodiment of the invention is constructed with an opening 110 in flexible sheet 92 to expose a patella of a knee to which the brace 90 is applied to atmosphere and to not inhibit movement of the knee in the preferred direction of freedom of movement.

The brace 90 is placed loosely around a knee 120 having a patella 122 and is set in position. The brace 90 is in the proper initial position when the patella 122 is surrounded by opening 110 so that the patella 122 is exposed to the atmosphere. Straps 96 and 97 are tightened sufficiently to hold brace 90 in its proper position and the inflatable chamber 94 is inflated using pump 108 connected to valve 106. When the proper pressure is reached, straps 96 and 97 are tightened to hold the brace 90 firmly in position. Here, again, the inflatable chamber 94 becomes quite rigid when it is inflated so that the elements of the knee 120 needing support will receive it. At the same time, abrasion of the knee 120 will be avoided because the inflatable chamber 94 is enclosed in the soft, flexible sheet 92.

ANKLE BRACE

In the embodiment of FIGS. 14 through 17, a brace 130 is to be used on an ankle 150. Brace 130 is seen to comprise a flexible sheet 132 of silicone polymer or similar material, and an inflatable chamber 134 having a pair of enlarged ends 136 and 138 connected by means of a narrow channel 140. The inflatable chamber 134 is formed of soft pliable material such as is used in inner tubes for bicycle tires which are flexible when not inflated and quite rigid when inflated. A valve 141 is connected to the inflatable chamber 134 and is adapted to receive a pump 142. Valve 141 is of the type which closes to prevent deflation when the pump 142 is removed. Straps 144 and 146, which are preferably provided with VELCRO fasteners, are used to hold the brace 130 on the ankle 150.

Figure 16:
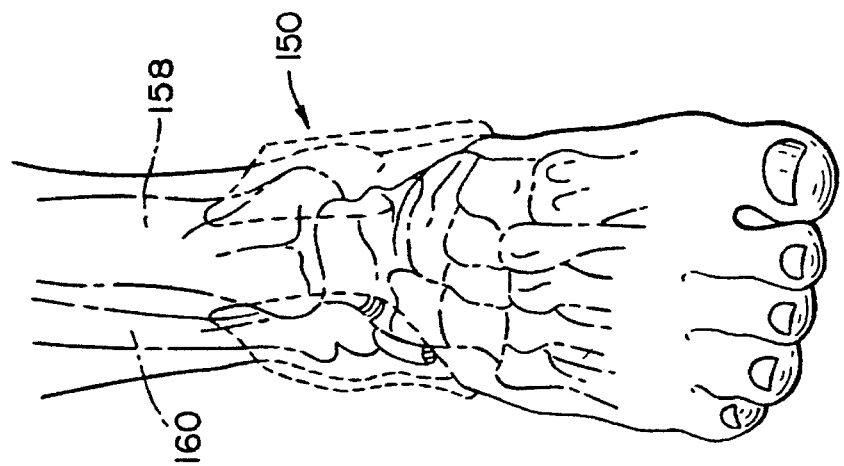
FIG. 16 is a view similar to that of FIG. 15 with the brace removed showing the position of the support member in dashed lines.
Figure 17:
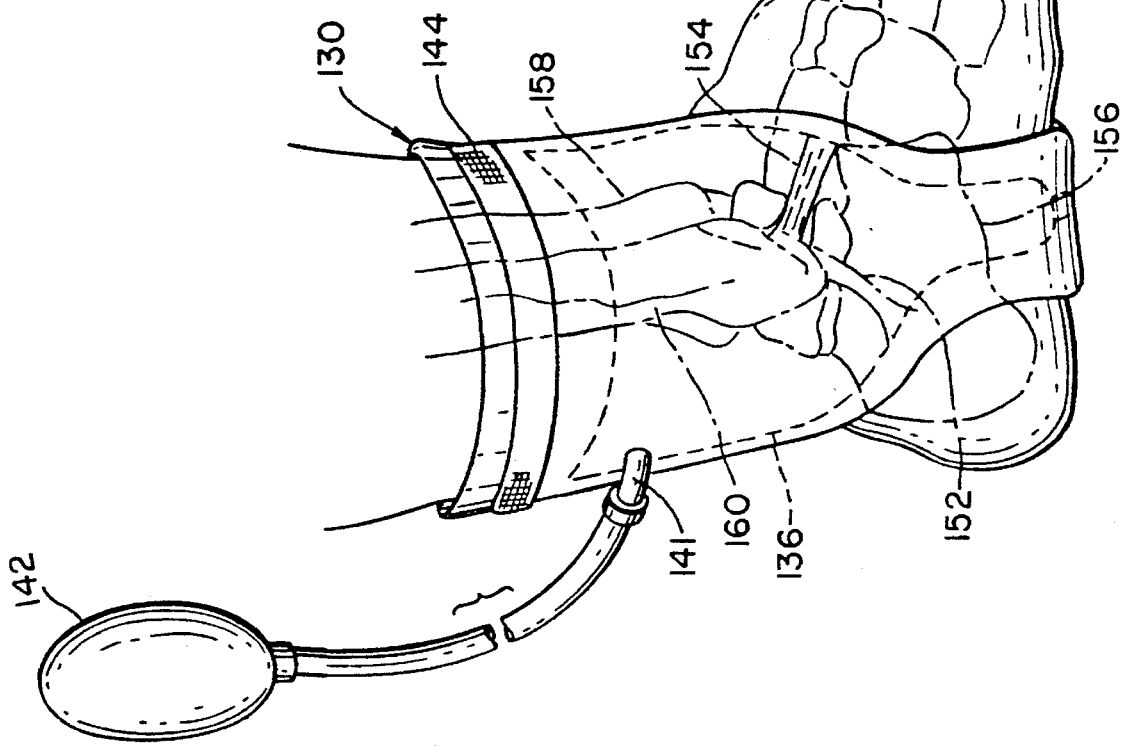
FIG. 17 is a partially opened view of the ankle of FIG. 16, slightly enlarged, showing the interior of the ankle with the support member in dashed lines.

In FIG. 17, ankle 150 is seen to comprise a calcaneo fibular ligament 152, an anterior talo fibular ligament 154 and a talus 156. The ankle 150 is connected to a tibia 158 and a fibula 160 to form the joint between the foot and the leg. The brace 130 is utilized to support the ankle 150 and the leg so that the joint will not be stressed during motion of the leg such as in walking. The brace 130 serves to support the ankle 150 so that the leg and foot move as a unit without flexure between them. FIG. 16 is a front view of the ankle 150 of FIG. 17.

In use, the brace 130 is loosely applied to the ankle 150 and the brace 130 is properly positioned. Then, the pump 142 is connected to valve 141 and the inflatable chamber 134 is inflated. When the proper amount of inflation is attained, the straps 144 and 146 are tightened and pump 142 is disconnected from valve 141 which closes so that chamber 134 remains inflated.

The inflatable chamber 134 performs the same function as has been described heretofore. It is soft and pliable when uninflated but is substantially rigid when inflated so as to render sufficient support with slight flexing under stress. The flexible sheet 132 serves to provide a soft, flexible surface contact with the ankle 150 to prevent abrasion.

ALTERNATE CONSTRUCTION FOR SUPPORT FOR CRUCIATE LIGAMENT DAMAGE

Figure 19:
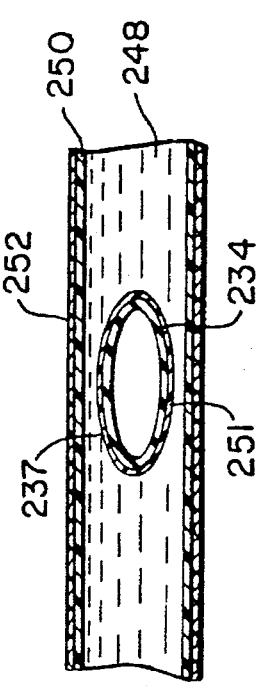
FIG. 19 is a cross-sectional view similar to FIG. 2, taken along line 19—19 of FIG. 18.
Figure 18:
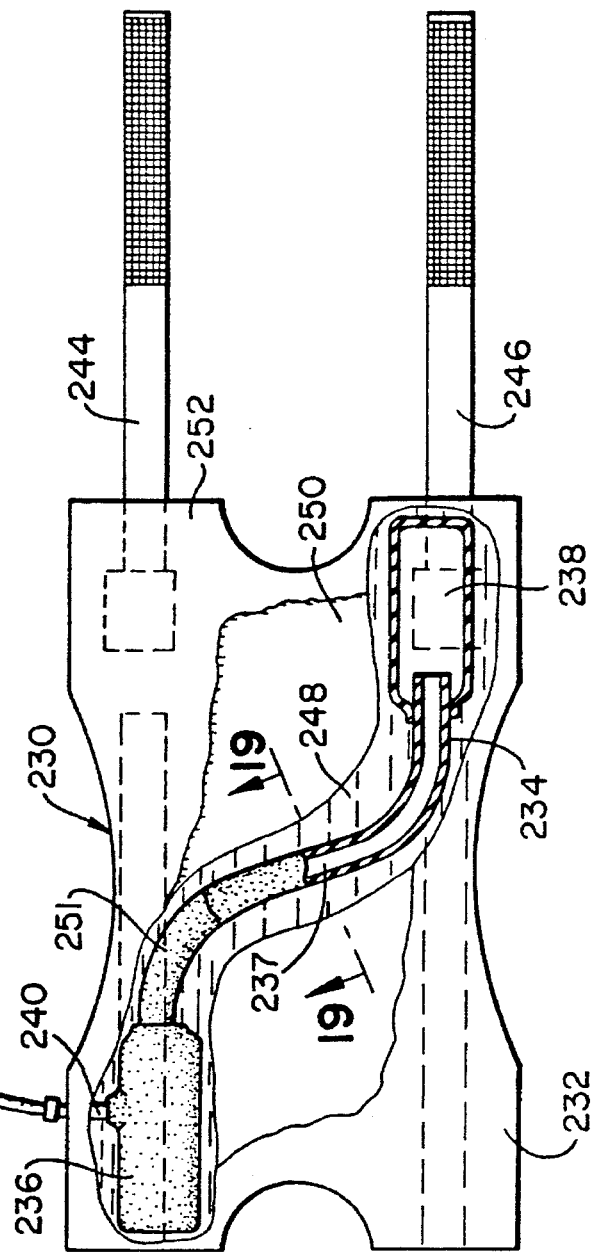
FIG. 18 is a plan view similar to FIG. 1, showing an alternate construction of the flexible member of the brace.

FIGS. 18 and 19 illustrate an alternate construction for the embodiment of FIGS. 1 through 6. In particular, FIG. 18 is similar to FIG. 1 and FIG. 19 is similar to FIG. 2; however, in the present embodiment, the flexible sheet includes an alternate construction which is illustrated in FIGS. 18 and 19. While the present construction of the flexible sheet is described as an alternate to the flexible sheet of the embodiment of FIGS. 1 through 6, it will be apparent that a similar alternate construction may be employed in connection with any of the embodiments of the invention shown and described herein.

Thus, in FIG. 18, a brace 230 is provided for use in connection with a knee having cruciate ligament damage. Brace 230 is seen to comprise a flexible sheet 232, an inflatable chamber 234 within the flexible sheet 232 and a pair of straps 244 and 246 including hook and loop fasteners, such as VELCRO fasteners. Flexible sheet 232 includes a fluid core 248 contained within a casing 250 which, itself, is surrounded by a cover 252. The construction of the flexible sheet 232 renders the flexible sheet 232 highly conformable so as to be juxtaposed appropriately with the knee in a ready manner. In the preferred construction, the core 248 is a polymeric gel-like material such as a silicone gel, the casing 250 is a conformable synthetic polymeric material which is impervious to the fluid material of the core 248, such as polyethylene, and the cover 252 is a textile material which is conformable and comfortable against the skin, such as LYCRA. The cover 252 is soft and nonabrasive so as to minimize discomfort or damage to the skin when the brace 230 is applied to a patient. The inflatable chamber 234 is formed of soft rubber or a similar material and preferably includes a reinforcing outer jacket 251 for added strength and shape retention. Jacket 251 is constructed of a synthetic polymeric material such as polyvinyl chloride or a similar material. Upon inflation, the inflatable chamber 234, along with jacket 251, will become rigid enough to support the injured portions of the body without damage.

Brace 230 is applied to the knee of the patient in the same manner as described above in connection with brace 30. Inflatable chamber 234 includes a sinuous medial section 237 and two enlarged chambers 236 and 238, one at each end of the sinuous medial section 237. Inflatable chamber 234 is inflated by means of a pump 242 which is connected to a valve 240 mounted in inflatable chamber 234. Valve 240 closes when the pump 242 is removed so as to maintain the required air pressure within the inflatable chamber 234.

The brace 230 operates in the same manner as brace 30, the installation and operation of which has been described in detail hereinabove. The construction of the flexible sheet 232 of brace 230, as shown and described herein as an alternate to the construction of the flexible sheet 32 of brace 30, also can be employed as an alternative construction for the flexible sheets of braces 60, 90 and 130.

ALTERNATE CONSTRUCTIONS FOR SUPPORT FOR CRUCIATE LIGAMENT DAMAGE UTILIZING AT LEAST TWO INFLATABLE SINUOUS MEMBERS

Figure 20:
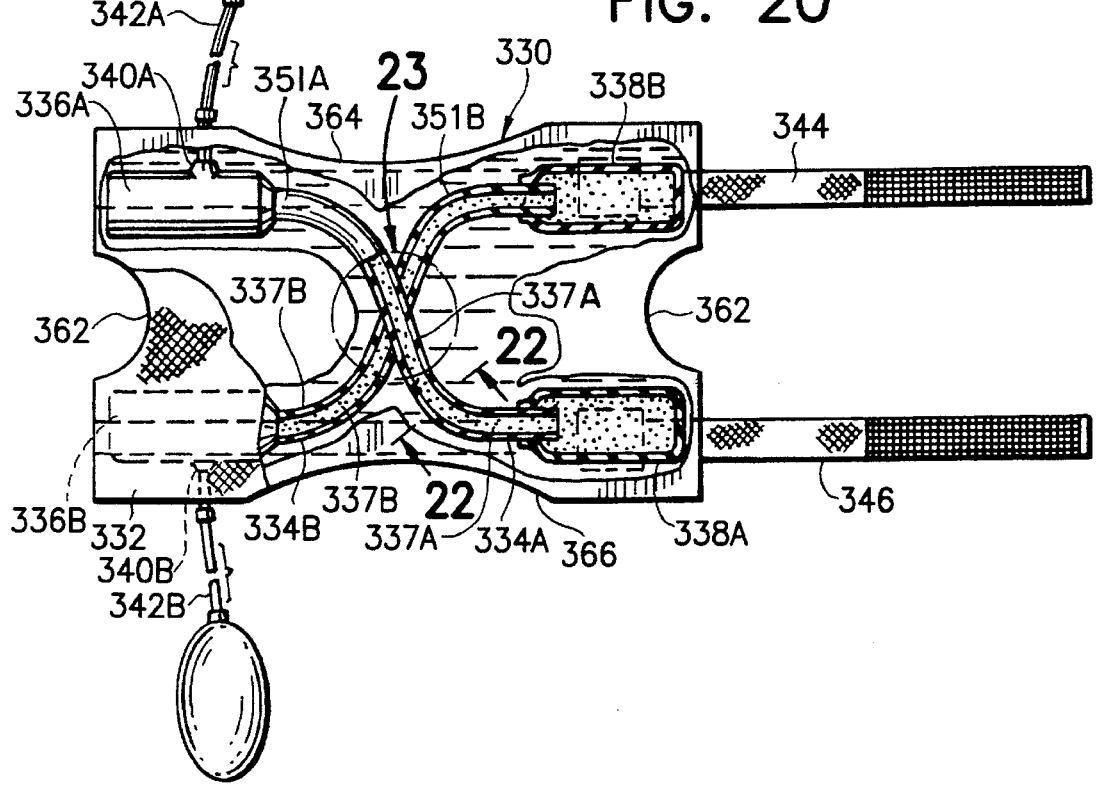
FIG. 20 is a plan view similar to that of FIG. 1 and FIG. 18 showing an alternate construction wherein there are two independent, flexible members of the brace which substantially follow the paths of the cruciate ligaments of the knee.
Figure 21:
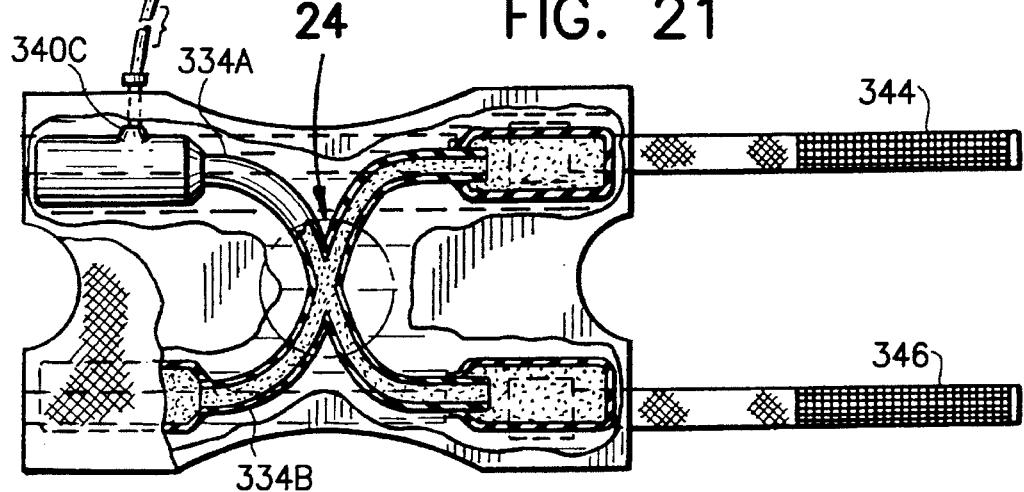
FIG. 21 is a plan view similar to that of FIG. 20 wherein the two flexible members of the brace intercommunicate to permit the flexible members to be inflated from a single source.
Figure 22:
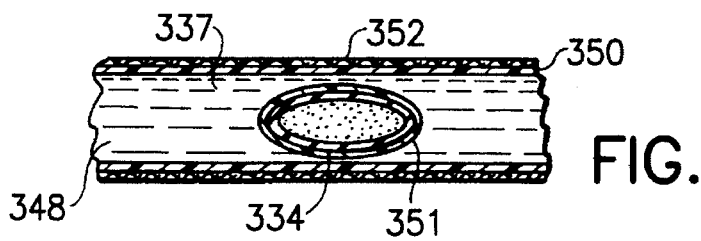
FIG. 22 is an enlarged cross-section taken along the line 22—22 of FIG. 20, viewed in the direction of the arrows.

FIGS. 20 through 28 illustrate alternate constructions for the embodiments of FIGS. 1 through 6 and FIGS. 18 and 19. In particular, FIGS. 20 and 21 are similar to FIGS. 1 and 18. The present embodiment illustrated in FIGS. 20 through 28 constitutes further alternates to the earlier described embodiments for correcting cruciate ligament damage or weakness. While the present construction of the braces of FIGS. 20 and 21 is directed, in particular, to the correction of the effects of cruciate ligament damage and weakness, it can be seen that a similar construction may be employed in connection with the other embodiments of the invention shown and described herein.

Thus, in FIG. 20, a brace 330 is provided for use in connection with a knee having cruciate ligament damage. Brace 330 is seen to comprise a flexible sheet 332, two inflatable chambers 334A and 334B within the flexible sheet 332 and a pair of straps 344 and 346 including hook and loop fastners, such as VELCRO fasteners. Flexible sheet 332 includes a fluid core 348 contained within a casing 350 which, itself, is surrounded by a cover 352. The construction of the flexible sheet 332 renders it highly conformable so as to be juxtaposed appropriately with the knee in a ready manner. In this preferred construction the core 348 is a polymeric gel-like material such as a silicone gel, the casing 350 is a conformable synthetic polymeric material which is impervious to the fluid material of the core 348, such as polyethylene, and the cover 352 is a textile material which is conformable and comfortable against the skin, such as LYCRA. The cover 352 is soft and nonabrasive so as to minimize damage to the skin when the brace 330 is applied to the patient. The inflatable chambers 334A and 334B are formed of soft rubber or a similar material and preferably include reinforcing outer jackets 351A and 351B constructed of a synthetic polymeric material such as polyvinyl chloride or a similar material. Upon inflation, the inflatable chambers 334A and 334B will become rigid enough to support the injured portions of the body without damage, generally along paths corresponding to the paths of the anterior and posterior cruciate ligaments.

Brace 330 is applied to the knee of the patient in the same manner as described above in connection with braces 30 and 230. Inflatable chambers 334A and 334B respectively include sinuous medial sections 337A and 337B and two enlarged chambers 336A and 338A and 336B and 338B, there being an enlarged chamber 336 and 338, one at each end of the sinuous medial sections 337A and 337B, respectively denominated 336A and 338A and 336B and 338B. Inflatable chamber 334A is inflated by means of a pump 342A and inflatable chamber 334B is inflated by means of a pump 342B. Each pump is connected to a valve which valves are denominated 340A and 340B and are respectively mounted in inflatable chambers 334A and 334B. The respective valves 340A and 340B close when the pumps 342A and 342B are removed so as to maintain the required air pressure within each respective inflatable chamber.

Figure 26:
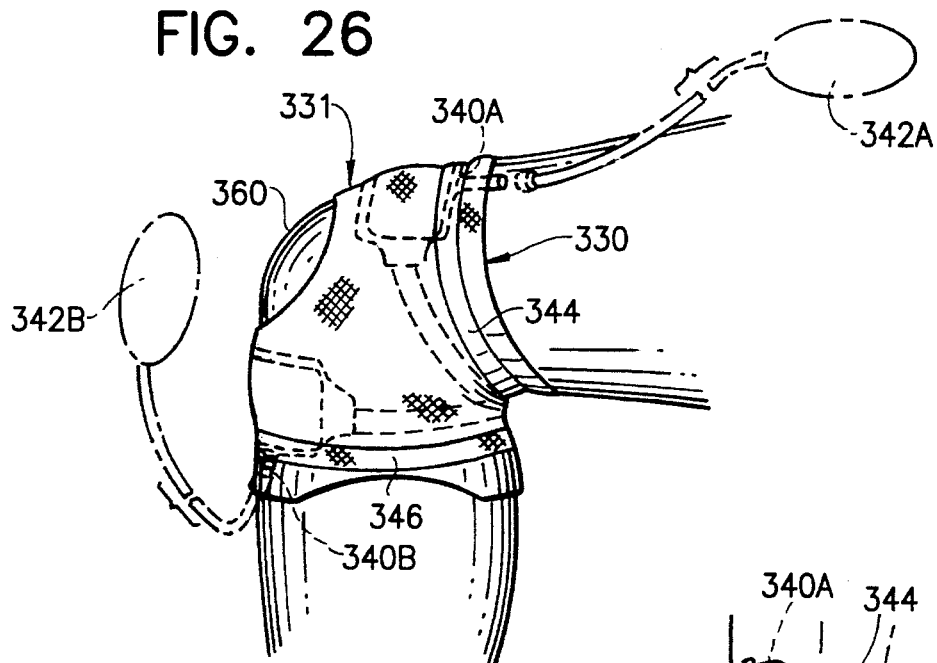
FIG. 26 is a view similar to that of FIG. 4 of a medial view of a flexed knee showing the brace of FIG. 20 applied thereto.
Figure 27:
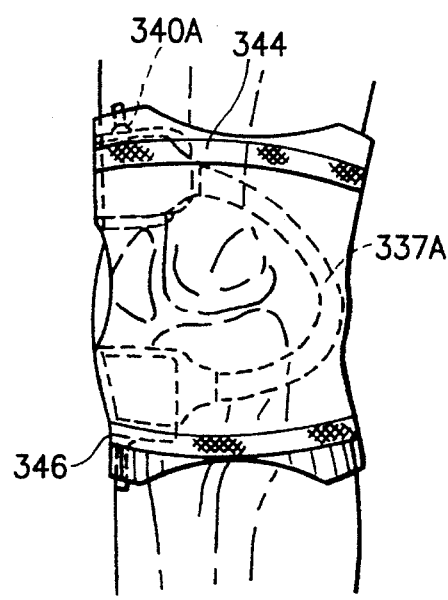
FIG. 27 is a view similar to that of FIG. 5 of a medial view of the knee of FIG. 20 in its extended position.
Figure 28:
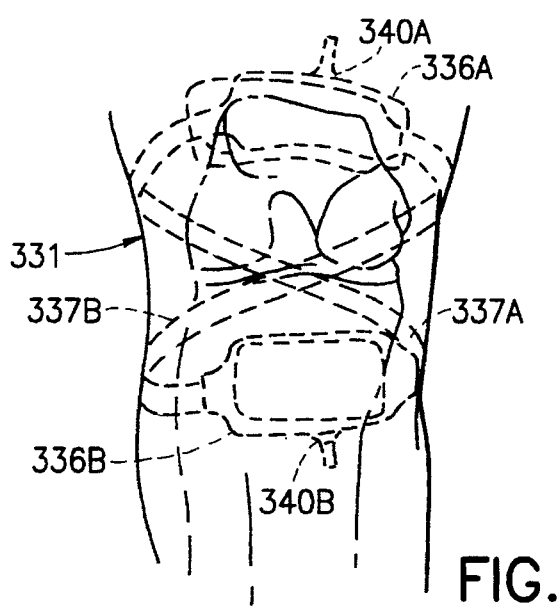
FIG. 28 is a view similar to that of FIG. 6 of an anterior view of the knee of FIG. 20 in its flexed position (patella not shown).

FIG. 26 is similar to FIG. 4 and illustrates a knee 331 in its flexed position with brace 330 applied thereto. The patella 360 of knee 331 is exposed to the atmosphere to minimize the effort of walking with the brace 330 affixed. This exposure of the patella 360 is accomplished by providing shaped areas 362 in sheet 332 (see FIG. 20). A pair of shaped areas 364 and 366 serves to accommodate for smooth application of the brace to the corresponding portions of the knee 331. Straps 344 and 346 are, preferably equipped with hook and loop fasteners, such as those commonly known as VELCRO fasteners and are used to hold brace 330 in place on knee 331.

Figure 23:
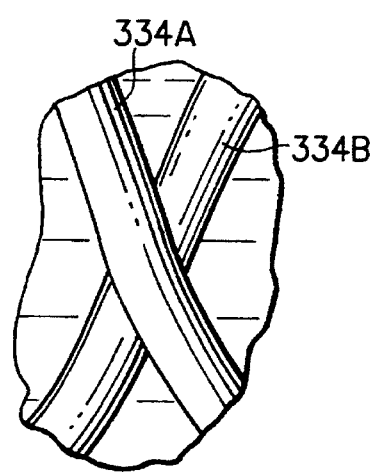
FIG. 23 is an enlarged view of the area designated by the arrow 23 of FIG. 20 showing the construction of the brace wherein the flexible members cross.
Figure 24:
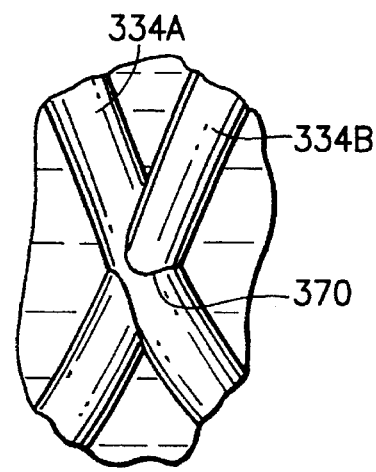
FIG. 24 is an enlarged view, similar to that of FIG. 23 of the area designated by the arrow 24 of FIG. 21 showing the construction of the brace wherein the flexible members intercommunicate.
Figure 25:
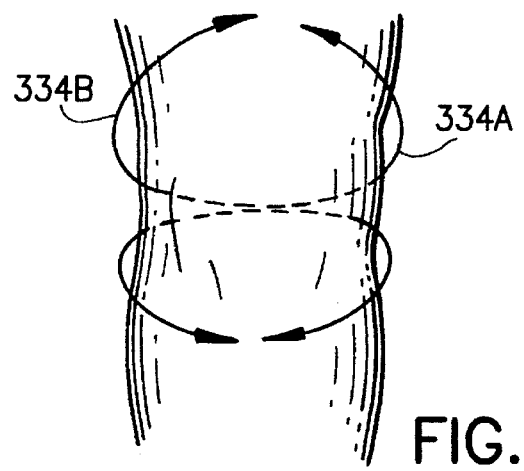
FIG. 25 is a diagrammatic view of the paths of the support elements when the brace is applied to a knee to correct cruciate ligament weakness.

The embodiment of FIGS. 21 and 24 is very similar to that of FIG. 20 and FIG. 23 which has been described just above. All of the elements of FIG. 20 are used in the embodiment of FIG. 21 except for one difference. In the embodiment of FIG. 20, the sinuous inflatable chambers 334A and 334B are independent preferably and are inflated by means of two pumps 342A and 342B, respectively. In the embodiment of FIG. 21, the sinuous inflatable chambers 334A and 334B intercommunicate at point 370 (FIG. 24) and both of the inflatable chambers are inflatable by means of a single pump 342C which inflates the chambers through valve 340C. The operations of the pump 342C and the valve 340C are identical to that previously described.

The salient difference between the embodiments of FIGS. 20 and 21 resides in the fact that in the case of the embodiment of FIG. 20, different pressures may be used in the two inflatable chambers. This permits the doctor to adjust the pressures applied to the cruciate ligaments separately. Thus, if one ligament is injured more than the other, the doctor is able to adjust the pressures to obtain a maximum treatment. On the other hand, if the damage difference between the ligaments of the knee is very minor, one can use the embodiment of FIGS. 21 and 24 and utilize a single pump to accomplish the desired corrective result.

The inflatable chambers follow the paths of the cruciate ligaments. One of them follows that of the anterior cruciate ligament and the other follows the path of the posterior cruciate ligament. The chambers cross each at a location corresponding to the same portion of the knee at which the cruciate ligaments cross.

METHOD OF SUPPORTING JOINTS

The method of the invention has been discussed as each of the apparatus embodiments has been discussed. It comprises utilizing at least one inflatable chamber which is enclosed in a soft flexible sheet. The inflatable chamber is flexible when uninflated and is substantially rigid when inflated. The sheet is positioned around the body joint so that when the inflated chamber is inflated the joint will be supported such that there is freedom of movement in a first selected direction and movement is essentially precluded in a second selected direction.

It is within the scope of the invention to utilize a single pump to inflate the sinuous inflatable chambers of FIG. 20. This may be accomplished by inflating one inflatable chamber, removing the pump and inflating the other inflatable chamber.

It should be noted that the valves used in the various embodiments of the invention are of the normally closed type such as are used on automobile and bicycle tires. These valves close to preclude deflation when the pump is disconnected from the valve.

While particular embodiments of the invention have been shown and described, it is apparent to those skilled in the art that modifications are possible without departing from the spirit and scope of the invention as set forth in the subjoined claims.

I claim:

1. A brace for supporting a weakened joint of the body, the weakened joint being a knee joint wherein both the anterior cruciate ligament and the posterior cruciate ligament are absent or have been repaired, so as to permit translation of the knee joint while restraining movement of the knee joint in directions which would tend to strain the cruciate ligaments to thereby support the weakened knee joint against movement of the knee joint in said directions and concomitant further injury to the knee joint, the brace comprising:

a flexible sheet adapted to be applied to the knee joint so as to protect the weakened knee joint from abrasion while permitting translation of the knee joint;

two inflatable chambers contained within the flexible sheet, each of said chambers including a medial section having a generally sinuous shape for juxtaposition with the weakened knee joint along a corresponding generally helical path of each of the cruciate ligaments around the knee joint to establish two corresponding generally helical paths around the knee joint as determined by the sinuous shapes of the inflatable chambers when the brace is applied to the weakened knee joint, one of said two helical paths corresponding to the path of the anterior cruciate ligament and the other of said two helical paths corresponding to the path of the posterior cruciate ligament;

said inflatable chambers being flexible when deflated, for conforming to said two generally helical paths around the knee joint, and being relatively stiff when inflated for contacting and supporting the weakened knee joint along said two generally helical paths around the knee joint such that anterior and posterior translations of the knee joint are permitted and motion of the knee joint in said directions which would place a strain on the cruciate ligaments is restrained;

means for holding the brace firmly in place when applied to the knee joint, with the inflatable chambers following the two generally helical paths around the weakened knee joint; and means for selectively inflating the inflatable chambers subsequent to applying the brace to the knee joint such that upon application of the brace to the knee joint and subsequent inflation of the inflatable chambers the weakened knee joint is supported with anterior and posterior translation of the knee permitted by virtue of the flexibility of the flexible sheet, while movement in said directions which would tend to strain the anterior and posterior cruciate ligaments is restrained by virtue of the stiffness and shape of the inflated chambers.

2. The invention in claim 1 wherein each inflatable chamber includes enlarged end sections integral with the medial section, there being one such enlarged section at each end of each medial section.

3. The invention of claim 2 wherein at least a portion of the medial portion of at least one of the inflatable chambers is lined with a reinforcing mesh to provide additional support to the weakened joint without inhibiting the flexibility of the inflatable chamber.

4. The invention of claim 3 wherein the flexible sheet is shaped to provide an opening therein to expose the patella of the knee to the atmosphere when the brace is applied to the knee.

5. The invention of claim 3 wherein the inflatable chambers cross each other.

6. The invention of claim 3 wherein the inflatable chambers are connected to permit both chambers to be inflated simultaneously from a single inflating source.

7. The invention of claim 1 wherein the means for holding the brace firmly in place comprises at least two straps.

8. The invention of claim 7 wherein the straps are provided with hook and loop fasteners.

9. The invention of claim 1 including a valve connected to each inflatable chamber for selectively controlling the inflation and deflation of the inflatable chambers.

10. The method of supporting a weakened knee joint in which either or both the anterior cruciate ligament and the posterior cruciate ligament is absent or weakened or has been repaired, so as to permit anterior and posterior translation of the knee joint while restraining movement of the knee joint in directions which would tend to strain the cruciate ligaments to thereby support the weakened knee joint against movement in said directions and concomitant further injury to the knee joint, the method comprising:

wrapping a flexible sheet having two inflatable chambers of sinuous shape contained therein around the knee joint;

positioning the flexible sheet such that the inflatable chambers follow two corresponding generally helical paths around the knee joint;

one of said two helical paths corresponding to the path of the anterior cruciate ligament and the other of said two helical paths corresponding to the path of the posterior cruciate ligament;

securing the wrapped positioned flexible sheet firmly around the knee joint; and inflating the inflated chambers so that the rigid conditions in contact with the knee joint along the generally helical paths around the knee joint such that the knee joint is supported to permit anterior and posterior translations of the knee joint while restraining movement of the knee joint in said direction which would tend to strain the anterior and posterior cruciate ligaments.

* * * * *